US011130978B2

(12) United States Patent
Aux

(10) Patent No.: US 11,130,978 B2
(45) Date of Patent: *Sep. 28, 2021

(54) METHODS FOR STARCH HYDROLYSIS

(71) Applicant: Syngenta Participations AG, Basel (CH)

(72) Inventor: George W. Aux, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/874,292

(22) Filed: May 14, 2020

(65) Prior Publication Data

US 2020/0270663 A1  Aug. 27, 2020

Related U.S. Application Data

(60) Continuation of application No. 16/519,707, filed on Jul. 23, 2019, which is a division of application No. 15/729,011, filed on Oct. 10, 2017, now Pat. No. 10,400,258, which is a division of application No. 12/395,180, filed on Feb. 27, 2009, now Pat. No. 9,816,119.

(60) Provisional application No. 61/032,773, filed on Feb. 29, 2008.

(51) Int. Cl.
*C12P 19/14* (2006.01)
*C12P 7/10* (2006.01)

(52) U.S. Cl.
CPC ............... *C12P 19/14* (2013.01); *C12P 7/10* (2013.01); *Y02E 50/10* (2013.01)

(58) Field of Classification Search
None
See application file for complete search history.

(56) References Cited

U.S. PATENT DOCUMENTS

| 5,525,154 | A | 6/1996 | Hagenimana et al. |
| 6,346,400 | B1 | 2/2002 | Caboche |
| 7,102,057 | B2 | 9/2006 | Lanahan et al. |
| 7,727,726 | B2 | 6/2010 | Cates |
| 7,914,993 | B2 | 3/2011 | Batie et al. |
| 8,507,231 | B2 | 8/2013 | Abbas et al. |
| 10,689,679 | B2 * | 6/2020 | Aux .................. C12P 7/10 |
| 2003/0125534 | A1 | 7/2003 | Callen et al. |
| 2003/0135885 | A1 | 7/2003 | Lanahan et al. |
| 2004/0018607 | A1 | 1/2004 | Callen et al. |
| 2008/0289066 | A1 | 11/2008 | Lanahan et al. |

FOREIGN PATENT DOCUMENTS

WO     2008080093     7/2008

OTHER PUBLICATIONS

Atichokudomchai et al., Carbohydrate Polymers, 2006, 64, 582-588.
O'Dea et al., Am. J. of Clinical Nutrition, vol. 34, Oct. 1981, pp. 1991-1993.
Konsula et al., Process Biochem., vol. 39, 2004, pp. 1745-1749.
Bijttebier et al, Biologia, vol. 63 (6), pp. 989-999 (2008).
Sun et al., Molecules, vol. 15, pp. 5162-5173 (2010).
Allen et al., "Multimolecular Substrate Reactions Catalyzed by Carbohydrases; Aspergillus oryzae a-Amylase Degradation of Maltooligosaccharides," Biochemistry, vol. 17, No. 12 (1978) pp. 2338-2344.
Allen et al., "Model for Carbohydrase Action: Aspergillus oryzae a-Amylase Degradation of Maltotriose", Biochemistry, vol. 17, No. 2 (1978) pp. 2345-2350.
Altichokudomchai, "Reaction Pattern of a Novel Thermostable a-amylase", Carbohydrate Polymers, vol. 64 (2006) pp. 582-588.
Banks et al., "Studies on Starch-Degrading Enzymes" Carbohydrate Research, 12, (1970) pp. 79-87.
Chiang et al., "Purification and Characterization of a Thermostable alpha-Amylase from Bacillus licheniformis", Starch, 31, (1979) Nr. 3, pp. 86-92.
Conrad et al., Hybrid Bacillus amyloliquefaciens X Bacillus lichenformis a-Amylases Contruction, properties and sequence determinants, Eur. J. Biochem., vol. 230 (1995), pp. 481-490.
Heitmann et al., "Characterization of three different potato starches and kinetics of their enzymatic hydrolysis by an a-Amylase", Enzyme and Microbial Technology, vol. 20 (1997), pp. 259-267.
Kennedy et al., "Characteristics of alpha-Amylase K, a Novel Amylase from a Strain of Bacillus subtilis", Starch, 31 (1979) pp. 93-99.
MacGregor et al., "The action of germinated barley alpha-amylases on linear maltodextrins", Carbohydrated Research vol. 227 (1992) pp. 301-313.
MacGregor et al., Models for the action of barley alpha-amylase isozymes on linear substrates, Carbohydrate Research, vol. 257 (1994) pp. 249-268.
Marchal et al., "Effect of Temperature on the Saccharide Composition Obtained after a-Amylolysis of Starch", Biotechnology and Bioengineering, vol. 63 (1999) pp. 344-355.
Nakakuki et al., "Action Patterns of Various Exo-Amylases and the Anomeric Configurations of their Products", Carbohydrate Research, vol. 128 (1984) pp. 297-310.
Robyt et al., "Action Pattern and Specificity of an Amylase from Bacillus subtilis", Archives of Biochemistry and Biophysics, vol. 100 (1963) pp. 451-467.

(Continued)

*Primary Examiner* — Hope A Robinson
(74) *Attorney, Agent, or Firm* — Michelle Lewis

(57) ABSTRACT

The presently disclosed subject matter provides a process for starch liquefaction using at least two classes of α-amylase enzymes, wherein the starch hydrolysis pattern from at least two of these classes is different. At least one class of enzyme is provided to the liquefaction process in the form of transgenic plant material expressing at least one class of α-amylase enzyme or is provided in the form of a purified or partially-purified α-amylase enzyme preparation. The second or subsequent class(es) of α-amylase enzymes may be provided in the form of additional transgenic plant material expressing the second or subsequent class(es), or may be provided in the form of a second or subsequent purified or partially-purified α-amylase enzyme preparation.

14 Claims, No Drawings

(56) References Cited

OTHER PUBLICATIONS

Robyt, "The Action Pattern of Porcine Pancratic a—Amylase in Relationship to the Substrate binding Site of the Enzyme", The Journal of Biological Chemistry, vol. 245, No. 15 (Aug. 1970) pp. 3917-3927.
Sano et al., Subsite Structure and Action Mode of the a-Amylase from Thermoactinomyces vulgaris, Agric. Biol. Chem., vol. 49 (1985) pp. 2843-2846.
Kondo et al. "Product Distribution in Amylase-Catalyzed Hydrolysis of Amylose", J. Biochem., vol. 87 No. 4 (1980) pp. 1053-1070.
Kwiatkowski et al., "Modeling the process and costs of fuel ethanol production by the corn dry-grind process," Industrial Crops and Products, 23 (2006) 288-296.
Brumm et al., "Purification and Characterization of the Commercialized, Cloned Bacillus Megaterium a-Amylase: Part II: Transferase Properties, Starch", (1991) 43, Nr. 8, pp. 319-323.

\* cited by examiner

METHODS FOR STARCH HYDROLYSIS

RELATED APPLICATION INFORMATION

This application is a continuation of patent application Ser. No. 16/519,707 filed Jul. 23, 2019 (now U.S. Pat. No. 10,689,679), which is a divisional of U.S. patent application Ser. No. 15/729,011 filed Oct. 10, 2017 (now U.S. Pat. No. 10,400,258), which is a divisional of U.S. patent application Ser. No. 12/395,180 filed Feb. 27, 2009 (now U.S. Pat. No. 9,816,119), which claims the benefit of U.S. Provisional Patent Application No. 61/032,773 filed Feb. 29, 2008, the contents of which are incorporated herein by reference in their entirety.

FIELD OF THE INVENTION

This invention relates to processing starch from plant sources, particularly for the production of ethanol.

BACKGROUND OF THE INVENTION

Starch is a complex carbohydrate often found in the human diet. Plants are often used as a source for starch, which can be used to produce ethanol and other products. Plant starches are generally in a granular form, which is insoluble in water. Conventional plant starch processing methods often involve a starch gelatinization process, wherein aqueous starch slurry is heated so that the granular starch in the slurry swells and bursts, dispersing starch molecules into the solution. During the gelatinization process, there is a dramatic increase in viscosity. To enable handling during the remaining process steps, the starch must be thinned or "liquefied". This reduction in viscosity can be accomplished by enzymatic degradation in a process referred to as liquefaction. During liquefaction, the long-chained starch molecules are degraded into smaller branched and linear chains of glucose units (dextrins) by an enzyme, such as $\alpha$-amylase (i.e., $\alpha$-amylase).

Amylase is an enzyme that catalyzes the hydrolysis of starches into sugars. Amylases hydrolyze internal $\alpha$-1,4-glucosidic linkages in starch, largely at random, to produce smaller molecular weight maltodextrins. Amylases are of considerable commercial value, as they are used in the initial stages (liquefaction) of starch processing; in wet corn milling; in alcohol production; as cleaning agents in detergent matrices; in the textile industry for starch desizing; in baking applications; in the beverage industry; in oilfields in drilling processes; in inking of recycled paper; and in animal feed.

SUMMARY OF THE INVENTION

The presently disclosed subject matter provides a process for starch liquefaction and the production of ethanol using at least two classes of $\alpha$-amylase enzymes, wherein the starch hydrolysis pattern from at least two of these classes is different. In some embodiments, at least one class of enzyme is provided to the liquefaction process in the form of transgenic plant material expressing at least one class of $\alpha$-amylase enzymes. The second or subsequent classes of $\alpha$-amylase enzymes may be provided in the form of additional transgenic plant material expressing the second or subsequent class(es), or may be provided in the form of a purified or partially-purified $\alpha$-amylase enzyme preparation. Alternatively, two or more classes of $\alpha$-amylase enzymes may be provided as purified or partially-purified $\alpha$-amylase enzyme preparations.

Also provided is a process for the production of ethanol comprising, liquefying an aqueous slurry of starch-containing plant material in the presence of at least two classes of $\alpha$-amylase enzymes, wherein the starch hydrolysis pattern from at least two of these classes is different, and using the liquefact in a fermentation process to generate ethanol.

One embodiment of the invention is a process for starch liquefaction, the process comprising liquefying an aqueous slurry of starch-containing plant material in the presence of at least a first and a second class of $\alpha$-amylase enzymes, wherein the first class of $\alpha$-amylase enzymes exhibits a starch hydrolysis pattern that is different from the starch hydrolysis pattern of at least the second class of $\alpha$-amylase enzymes. The following embodiment may be carried out wherein the starch-containing plant material comprises a transgenic plant part comprising a polynucleotide encoding either the first or second class of $\alpha$-amylase enzymes or the transgenic plant may be engineered to express both enzymes. The process may also comprise a purified or partially-purified first and second class $\alpha$-amylase enzyme, wherein the process comprises one or more liquefaction steps that are performed under conditions sufficient for the first and second class $\alpha$-amylase enzymes to hydrolyze said starch-containing plant material. In another embodiment, it may be beneficial to add the first and second class enzymes into the slurry in a liquefaction step that is performed under conditions sufficient for the first and second classed of $\alpha$-amylase enzymes to hydrolyze said starch-containing plant material. In some embodiments the starch-containing plant material is derived from a plant selected from the group consisting of rice, barley, potato, sweet potato, canola, sunflower, rye, oats, wheat, corn, soybean, sugar beet, tobacco, Miscanthus grass, Switch grass, safflower, trees, cotton, cassava, tomato, sorghum, alfalfa and sugarcane.

Another embodiment presented in the current invention is a process for producing ethanol comprising liquefying an aqueous slurry of starch-containing plant material in the presence of at least a first and a second class of $\alpha$-amylase enzymes, wherein the first class of $\alpha$-amylase enzymes exhibits a starch hydrolysis pattern that is different from the starch hydrolysis pattern of at least the second class of $\alpha$-amylase enzymes to obtain a liquefact; and, fermenting the liquefact by yeast to obtain ethanol. The process may further comprise a saccharification step in the presence of a glucoamylase, wherein the saccharification step can be performed simultaneously with liquefaction and fermentation.

Another embodiment is a process for producing ethanol comprising raw starch fermentation of starch-containing plant material in the presence of at least a first and a second class of $\alpha$-amylase enzymes, wherein the first class of $\alpha$-amylase enzymes exhibits a starch hydrolysis pattern that is different from the starch hydrolysis pattern of at least the second class of $\alpha$-amylase enzymes.

DETAILED DESCRIPTION OF THE INVENTION

Embodiments of the invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Overview

The first step in the processing of grain to ethanol in the dry grind process involves the hydrolysis of starch mediated by α-amylases. Typical corn-to-ethanol conversion processes utilize an α-amylase enzyme derived from a bacterium of the genus *Bacillus* to liquefy starch-containing plant material (e.g., grain) in the presence of water. The liquefaction reaction involves heating a combination of ground grain and water beyond the grains' gelatinization point under slightly acidic conditions in the presence of an enzyme that will hydrolyze the linkage between the glucose units rendering a complex mixture of dextrins, sugars and other retrograde products.

Most α-amylase enzymes from the *Bacillus* genus have a pattern of hydrolysis yielding a characteristic composition of these breakdown products (i.e., "hydrolysates"). Another class of α-amylase enzymes has a novel pattern of starch hydrolysis and produces a very different combination of hydrolysates. The performance in terms of ethanol production and residual sugars/starch of the liquefied substrate produced with either class of α-amylases is very similar. Both classes of alpha-amylase enzymes are able to hydrolyse starch in a manner that supports ethanol production. However, while not bound by any particular theory or mechanism, it is believed that using the two different classes of α-amylase enzymes together in a liquefaction reaction will produce a substrate that will give higher concentrations of ethanol and less residual sugars/starch in a fermentation process than the use of either class alone.

Thus, described herein are methods for the liquefaction of starch-containing plant material using at least two different classes of α-amylase enzymes, wherein the process comprises liquefying an aqueous slurry of starch-containing plant material in the presence of at least a first and a second class of α-amylase enzymes, wherein the first class of α-amylase enzymes exhibits a starch hydrolysis pattern that is different from the starch hydrolysis pattern of at least the second class of α-amylase enzymes. By "starch hydrolysis pattern" is intended the collection of hydrolysates resulting from the enzymatic conversion of starch to sugar. While the activity of α-amylase is primarily hydrolytic, several amylase enzymes are known to have transglycosylation activity, resulting in the production of higher molecular weight oligosaccharides (see, for example, Thompson et al. (1997) Nucleic Acids Res. 25:4876-4882 and Rivera et al. (2003) Protein Engineering 16(7):505-514). Thus, for the purposes of the present invention, the starch hydrolysis pattern includes sugars resulting from hydrolysis as well as from transglycosylation.

In various embodiments, the first class of α-amylase, the second class of alpha amylase, or both, is provided in the form of transgenic plant material. In another embodiment, either the first or the second class of α-amylase enzymes, or both, is provided as a purified or partially-purified preparation of the α-amylase enzyme. In yet another embodiment, one class of α-amylase is provided as transgenic plant material expressing the α-amylase, and the other α-amylase is provided exogenously to the slurry as a purified or partially-purified preparation of the enzyme. It is to be understood that the terms "first" and "second" are used for purposes of distinguishing two different classes of enzymes, but is not related to the order in which each is used in a starch-conversion process.

Alpha-Amylase

The present invention relates to methods of starch hydrolysis using at least two different classes of alpha-amylase ("α-amylase") enzymes. As used herein, the term "amylase" encompasses enzymes (e.g., E.C. class 3.2.1.1) having α-amylase activity, for example, α-amylases capable of hydrolyzing internal α-1,4-glucan links in polysaccharides, including amylase enzymes capable of hydrolyzing starch to sugars at alkaline pHs or at acidic pHs. These enzymes have also been described as those effecting the exohydrolysis or endohydrolysis of 1,4-α-D-glucosidic linkages in polysaccharides containing 1,4-α-linked D-glucose units. Another term used to describe these enzymes is "glycogenase."

The α-amylase enzymes useful herein are characterized and classified according to the number and/or type of hydrolysis products resulting from liquefaction of starch-containing plant material in the presence of the α-amylase enzyme. For the purposes of the present invention, the type of hydrolysis product refers to the degree of polymerization (DP) of the product. For example, DP1 and DP2 refer to mono- and disaccharides, respectively; DP3 to DP9 refer to oligosaccharides containing three to nine monosaccharide units; and designations of DP10 or greater refer to polysaccharides containing 10 or more monosaccharide units. Hydrolysis products are considered to be in the "lower size range" if the DP is equal to or less than 30. Hydrolysis products are considered to be "higher size range" if the DP is greater than 30.

The starch hydrolysis pattern for an α-amylase enzyme can be determined using any number of techniques. In one embodiment, the hydrolysis pattern is characterized by analyzing the hydrolysis products using size exclusion chromatography as described in the Experimental Examples herein. In another embodiment, the hydrolysis pattern can be determined based on the method described in Robyt & French (1967) *Archives of Biochemistry and Biophysics* 100:451-467, optionally as modified in Atichokudomchai et al. (2006) *Carbohydrate Polymers* 64:582-588, or in MacGregor et al. (1992) Carbohydrate Res. 227:301-313; Nakakuki et al. Carbohydrate Res. 128 (1984) 291-310; Saito, N. Archives of Biochemistry and Biophysics 155, 290-298 (1973); Marchal et al. Biotechnology and Bioengineering, Vol 63, No. 3, May 5, 1999; Ivanova, et al. Applied Biochemistry and Biotechnology Vol 30, 1991. 193-202; and, Heitmann et al. Enzyme and Microbial Technology 20:259-267, 1997, each of which is herein incorporated by reference in its entirety.

The hydrolysis pattern is typically measured within a particular dextrose equivalent range. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100. In one embodiment, the hydrolysis pattern is measured when the DE is between 10 and 20, or between 10 and 15.

In the methods of the present invention, liquefaction of the starch-containing plant material is performed in the presence of at least two classes of α-amylase enzymes. In one embodiment, at least one class of α-amylase enzymes exhibits a starch hydrolysis pattern that is unimodal in distribution, and the other class exhibits a starch hydrolysis pattern that is bimodal in distribution. In another embodiment, liquefaction is performed in the presence of at least two different classes of α-amylase enzymes, wherein each class exhibits a different unimodal distribution. A "unimodal" distribution occurs when substantially all of the detectable hydrolysis products fall within a particular size range (e.g., higher or lower size ranges). Where the method employs at least two different unimodal classes of α-amylase enzymes, substantially all of the hydrolysis products from one class will fall into one size range, and substantially all of the hydrolysis products from the other class will fall into a different size range. By "substantially all" is intended at least about 90%, at least about 91%, at least about 92%, at least about 93%, at least about 94%, at least about 95%, at least about 96%, at least about 97%, at least about 98%, at least about 99%, or greater, of the detectable hydrolysis products fall within a particular size range. A "bimodal" distribution occurs when the hydrolysis products fall into at least 2 different size ranges. To be considered "bimodal," greater than 10% of the total detectable hydrolysis product must be represented in at least two different size ranges (i.e., at least 10% must be in one size range, and at least 10% must be in a different size range).

It is also contemplated that α-amylase enzymes will be identified that exhibit "multimodal" distribution patterns, where at least 10% of the total detectable hydrolysis product is represented in more than 2 size ranges, may exhibit a bimodal pattern with at least 10% of the total detectable hydrolysis products present in at least 2 size ranges that are different from the "high" and "low" patterns defined supra. In these embodiments, the size ranges may include, for example, any range from DP1 to greater than DP4000 (e.g., DP less than 10, DP less than 20, DP less than 40, DP less than 50, DP less than 100, DP1 to DP10, DP1-DP5, DP5-DP15, DP10-DP20, DP15-DP25, DP20-DP40, DP25-DP45, DP40-DP60, DP45-DP65, DP60-DP100, DP70-DP110, DP100-DP200, DP200-DP500, DP500-1000, DP1000-DP2000, DP2000-DP3000, DP3000-DP4000, DP greater than 500, DP greater than 600, DP greater than 700, DP greater than 1000, DP greater than 2000, DP greater than 3000, and DP greater than 4000). Such multimodal and alternative bimodal classes of α-amylase enzymes are useful in the present invention. However, unless otherwise specified, the term "bimodal" refers to a starch hydrolysis pattern in which at least 10% of the total detectable products are in the lower size range defined by DP less than or equal to 30, and at least 10% of the detectable products are in the higher size range defined by DP greater than 30.

Suitable α-amylases include naturally occurring α-amylases as well as recombinant or mutant amylases which are useful in liquefaction of starch. In one embodiment, the class of α-amylase enzymes exhibiting a unimodal starch hydrolysis pattern includes the α-amylase ("797GL3") described in Richardson et al. (2002) *J Biol Chem.* 277(29):26501-7 which is herein incorporated by reference in its entirety. In another embodiment, the unimodal α-amylase is the α-amylase ("D45") described in Atichokudomchai et al. (2006) *Carbohydrate Polymers* 64:582-588, herein incorporated by reference in its entirety. See also, US Patent Publication 2003/0125534 and U.S. Patent Publication 2004/0018607 (both are herein incorporated by reference) which describe numerous other α-amylase enzymes that share sequence identity to the 797GL3, BD12870 and D45 enzymes. In another embodiment it is expected that α-amylases derived from the microorganism order Thermococcales demonstrate a unimodal hydrolysis pattern.

Suitable classes of α-amylase enzymes exhibiting a bimodal distribution of hydrolysis products include, for example, the α-amylases derived from *Bacillus* sp. (e.g., *Bacillus licheniformis* and *Bacillus amyloliquefaciens* α-amylase enzymes).

The hydrolysis pattern can also be determined for any number of known amylase enzymes using the methods described herein. Amylases are produced by a wide variety of microorganisms including *Bacillus* and *Aspergillus*, with most commercial amylases being produced from bacterial sources such as *Bacillus licheniformis, Bacillus amyloliquefaciens, Bacillus subtilis*, or *Bacillus stearothermophilus*. Amylase enzymes falling into a desirable hydrolysis "class" can then be used in the methods of the invention.

Techniques for producing variant amylases are also known in the art. Such techniques could be utilized to alter the hydrolysis properties of known amylase enzymes to suit the needs of the present invention.

Additionally, polynucleotides encoding the characterized α-amylases described herein or otherwise known in the art may be used to isolate homologous sequences from cultured organisms or environmental samples. In one embodiment, gene libraries generated from one or more α-amylase expressing microorganisms can be screened for amylase enzymes exhibiting a particular hydrolysis pattern. Methods for making and using organisms expressing α-amylase enzymes (for example, to produce fermentable substrates for the production of ethanol) are also provided in U.S. Patent Publication No. 2003/0135885, which is herein incorporated by reference in its entirety.

Enzyme Extracts

In various embodiments of the present invention, either the first or the second class of α-amylase enzymes, or both, is provided as a crude, purified or partially-purified preparation of the α-amylase enzyme. The exogenously-added α-amylase enzyme may be de novo synthesized, or may be isolated from an organism expressing the α-amylase enzyme prior to addition of the enzyme to the starch-containing plant material, or may be through the addition of a crude extract containing at least one enzyme useful in starch conversion.

An exogenously-added enzyme may be a crude, purified or partially-purified preparation of enzyme containing at least one class of α-amylase enzyme, but may also contain one or more additional α-amylase enzymes of the same or different class. The preparation may further comprise one or more additional enzymes useful in the starch conversion method, such as glucoamylase. A "partially-purified" enzyme preparation will contain one or more α-amylase enzymes, one or more additional enzymes useful in the starch conversion process, or may contain other buffers or stabilizing agents (e.g., glycerol). Furthermore, the partially-purified enzyme preparation may also be culture supernatant or crude extract collected from a cell population expressing and/or secreting the enzyme. The preparation may also be a lyophilized formulation of enzyme that is reconstituted upon addition to the starch-containing plant material.

Alpha-amylase enzymes can be expressed in and isolated from any number of eukaryotic and prokaryotic organisms. Appropriate expression cassettes, vectors, transformation, and transfection techniques for a particular organism of interest will be evident to one of skill in the art.

In one embodiment, bacterial cells, such as *E. coli, Streptomyces, Bacillus subtilis*; and various species within the genera *Escherichia, Pseudomonas, Serratia, Streptomyces, Corynebacterium, Brevibacterium, Bacillus, Microbacterium*, and *Staphylococcus* can be used as a host to express one or more classes of α-amylase enzymes encompassed herein. Methods for transformation of bacterial hosts are described in, for example, U.S. Patent Publication No. 2003/0135885.

In another embodiment, fungal hosts, such as fungal host cells belonging to the genera *Aspergillus, Rhizopus, Trichoderma, Neurospora, Mucor, Penicillium*, etc., such as yeast belonging to the genera *Kluyveromyces, Saccharomyces, Schizosaccharomyces, Trichosporon, Schwanniomyces*, etc. may be used. Transformation of fungus may be accomplished according to Gonni et al. Agric. Biol. Chem., 51:2549 (1987).

Another suitable host includes any number of eukaryotic cells, for example, insect cells such as *Drosophila* S2 and *Spodoptera* Sf9; animal cells such as CHO, COS or Bowes melanoma, C127, 3T3, CHO, HeLa and BHK cell lines. Any host can be used insofar as it can express the gene of interest. The American Type Culture Collection (www.atcc.org/) maintains cell lines from a wide variety of sources and many of these cultures can be used to generate a transgenic cell line capable of expressing an α-amylase enzyme. Transformation vectors appropriate for eukaryotic cells are available commercially such as pXT1, pSG5 (Stratagene) pSVK3, pBPV, pMSG, and pSVLSV40 (Pharmacia). Techniques for transformation and selection of transgenic eukaryotic cells are well known in the art.

Additional methods for generating an enzyme extract are described in, for example, Conrad et al. (1995) *Eur. J. Biochem.* 230, 481-490; Chiang et al. (1979) Starch 31 Nr.3, S.86-92; Schwardt, E. (1990) Food Biotechnology, 4(1), 337-351; Morgan and Priest (1981) Journal of Applied Bacteriology 50, 107-114; Laderman et al. (1993) Journal of Biological Chemistry Vol. 268, No. 32, pp. 24394-24401, each of which is herein incorporated by reference in its entirety.

Transgenic Plants

In one embodiment of the present invention, the starch-containing plant material comprises plant parts derived from at least one variety of a transgenic plant expressing a polynucleotide encoding an α-amylase enzyme. As used herein the term "transgenic" refers to plants that include an exogenous polynucleotide (e.g., gene) that is stably maintained in the transformed plant and is stably inherited by progeny in successive generations. The term "transgenic plant" can refer either to the initially transformed plant or to the progeny of the initially transformed plant. Techniques for transforming plants, plant cells or plant tissues can include, but are not limited to, transformation with DNA employing *A. tumefaciens* or *A. rhizogenes* as the transforming agent, electroporation, DNA injection, microprojectile bombardment, and particle acceleration. See, for example, EP 295959 and EP 138341. As used herein, the terms "plant material" or "plant part" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like. As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

In this embodiment, it is not necessary for the starch-containing plant material to be 100% transgenic for the α-amylase enzyme. Rather, it is only necessary for the plant material to contain an amount of amylase that is sufficient for the downstream use. For example, for fermentation purposes, a sufficient amount of amylase enzyme may be provided in the fermentation process by less than 100% amylase-expressing plant material. For example, a sufficient amount of amylase enzyme may be provided to the fermentation process when only about 0.1% of the plant material expresses amylase, or only about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%, of the plant material. However, it is contemplated that the percentage of plant material expressing the α-amylase could be as much as 100%, including, for example, about 25%, about 30%, about 35%, about 40%, about 50%, about 60%, about 65%, about 70%, about 80%, about 90%, about 95%, or about 99% of the plant material.

Where both classes of α-amylase enzymes are provided as transgenic plant material, each class of α-amylase may be expressed in the same plant variety, or may be expressed in different plant varieties. Where each amylase is expressed in different plant varieties, the transgenic plant material can be combined at a target ratio necessary to achieve a target level of each of the α-amylase enzymes necessary for optimal liquefaction. "Optimal liquefaction" can refer to the total amount of starch-derived product, as well as the variety of different starch-derived products resulting from hydrolysis of the starch-containing plant material. For example, the starch-derived products can include oligo- and polysaccharides having various chain lengths or having various branching patterns.

The amount of the starch-containing transgenic plant material can be adjusted to effect optimal liquefaction (i.e., by adjusting the amount of starch-digesting enzyme provided in the slurry). The amount can vary depending upon the plant material, the desired mixture of products in the starch liquefact, the desired speed of liquefaction, or upon a pre-selected liquefaction temperature. Optimal liquefaction will typically be determined by the downstream user (e.g., ethanol producer) and takes into account a variety of factors including, but not limited to, the level or expression of the amylase in the plant or plant part, the type of plant utilized, and processes involved in converting the starch-containing plant material to a useful product (e.g., food, feed, industrial alcohol, biofuel, fermentation product, etc.). For example, an ethanol production facility interested in utilizing a combination of α-amylase enzymes having different starch hydrolysis patterns, the target ratio necessary to achieve optimal liquefaction will take into account the chemical conversion and/or fermentation processes involved in converting the plant material to ethanol, including the reaction conditions, the level or activity of any exogenous enzymes (α-amylase or otherwise) that may be included in the process, the types of oligo- and polysaccharides desirable for feedstock, as well as any other materials required for each step in the conversion. One of skill in the art will understand how to determine the amount of amylase or amylase-expressing plant material to use for a particular downstream use.

Thus, in one embodiment, the starch-containing plant material comprises about 0.1% to about 99.9%, including about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, about 95%, about 97%, about 98%, and about 99%, plant material derived from plants expressing a first class of α-amylase and about 0.1 to about 99.1%, including about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25% about 30%, about 35%, about 40%, about 45%, about 50%, about 55%, about 60%, about 65%, about 70%, about 75%, about 80%, about 85%, about 90%, about 95%, about 97%, about 98%, and about 99%, plant material derived from plants expressing a second class of α-amylase, wherein the sum of the percentage of each plant variety equals 100% of the total plant material. The starch-containing plant material may further comprise about 0.1% to about 99.8%, including about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, about 95%, about 97%, about 98%, and about 99%, plant material derived from one or more additional varieties, which may or may not express an α-amylase enzyme (e.g., "wild-type" plant material, or plant material expressing one or more transgenes other than α-amylase).

The transgenic or non-transgenic starch-containing plant material can be derived from any plant, including but not limited to plants producing edible flowers such as cauliflower (*Brassica oleracea*), artichoke (*Cynara scolvmus*), and safflower (*Carthamus*, e.g. *tinctorius*); fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, *Juglans*, e.g. *regia*; peanut, *Arachis hypoaea*), orange (*Citrus*, e.g. *maxima*), peach (*Prunus*, e.g. *persica*), pear (*Pyra*, e.g. *communis*), pepper (*Solanum*, e.g. *capsicum*), plum (*Prunus*, e.g. *domestica*), strawberry (*Fragaria*, e.g. *moschata*), tomato (*Lycopersicon*, e.g. *esculentum*); leaves, such as alfalfa (*Medicago*, e.g. *sativa*), sugar cane (*Saccharum*), cabbages (such as *Brassica oleracea*), endive (*Cichoreum*, e.g. *endivia*), leek (*Allium*, e.g. *porrum*), lettuce (*Lactuca*, e.g. *sativa*), spinach (*Spinacia* e.g. *oleracea*), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*) yam (*Dioscorea*, e.g. *esculenta*), sweet potato (*Ipomoea batatas*); seeds, such as bean (*Phaseolus*, e.g. *vulgaris*), pea (*Pisum*, e.g. *sativum*), soybean (*Glycine*, e.g. *max*), wheat (*Triticum*, e.g. *aestivum*), barley (*Hordeum*, e.g. *vulgar*), corn (*Zea*, e.g. *mays*), rice (*Oryza*, e.g. *sativa*); grasses, such as *Miscanthus* grass (*Miscanthus*, e.g., *giganteus*) and switchgrass (*Panicum*, e.g. *virgatum*); trees such as poplar (*Populus*, e.g. *tremula*), pine (*Pinus*); shrubs, such as cotton (e.g., *Gossypium hirsutum*); and tubers, such as kohlrabi (*Brassica*, e.g. *oleracea*), potato (*Solanum*, e.g. *tuberosum*), and the like.

The starch-containing plant material may also comprise one or more varieties of plants having naturally-occurring genetic variability resulting in altered starch metabolism. Many such plants carry mutations in genes encoding isoforms of starch synthesis or starch degradation enzymes. For example, plants have been identified which are heterozygous or homozygous for one or more of the waxy (wx), amylose extender (ae), dull (du), horny (h), shrunken (sh), brittle (bt), floury (fl), opaque (o), or sugary (su) mutant alleles. See, for example, U.S. Pat. Nos. 4,428,972; 4,767,849; 4,774,328; 4789738; 4,789,557; 4,790,997; 4,792,458; 4,798,735; and 4,801,470, herein incorporated by reference. These plants can be used in their native form, or can be modified to exhibit one or more transgenes (e.g., amylase, or other commercially or agronomically useful transgenes) of interest.

Methods

The methods of the present invention are directed to a process for starch liquefaction, the process comprising liquefying an aqueous slurry of starch-containing plant material in the presence of at least a first and a second class of α-amylase enzyme, wherein the first class of α-amylase enzyme exhibits a starch hydrolysis pattern that is different from the starch hydrolysis pattern of at least the second class of α-amylase enzyme. The term "slurry" refers to a mixture of starch or a starch-containing material (e.g., milled corn) and an aqueous component, which can include, for example, water, deionized water, or a process water (i.e., backset, steam, condensate), or any combination thereof. As used herein the terms "liquefaction," "liquefy," "liquefact," and variations thereof refer to the process or product of converting starch to soluble dextrinized substrates (e.g., smaller polysaccharides). Liquefact can also be referred to as "mash." The products of this liquefaction can be concentrated and purified for food and other applications such as cleaning agents, textile agents, and animal feed. Herein, the term "biofuels" refers to any fuel derived from harvested plant parts. Biofuels comprise but are not limited to biodiesel, vegetable oils, bioalcohols (i.e. ethanol, methanol, propanol, butanol, etc.) and biogases (i.e. methane).

In one embodiment, the liquefact is further processed to produce ethanol. In one embodiment, the use of at least two different classes of α-amylase enzymes in the liquefaction process results in a substrate that leads to higher ethanol yields compared to the ethanol yield from starch-containing plant material that is exposed to only one class of α-amylase enzymes. When comparing the yield of ethanol from liquefact resulting from hydrolysis of starch-containing plant material exposed to various combinations of α-amylase enzymes, the comparison is performed within the same DE range for each "test" and "control" condition. For example, when comparing the yield of ethanol using a single class of α-amylase enzyme ("control") to the yield of ethanol using two different classes of amylase enzymes ("test"), the concentration of each class of α-amylase enzymes in the test group is adjusted to obtain a similar DE under similar hydrolysis conditions as the control α-amylase (where conditions are otherwise adjusted for optimum performance of each class of enzyme). See, for example, Experimental Example 3. In one embodiment, the comparison is performed at a DE between 10 and 15. Such an increase may be considered to be synergistic. For the purposes of the present invention, a "synergistic" increase in ethanol production is any increase in ethanol production that is higher than the ethanol production of either individual class of α-amylase alone, when measured within equivalent DE ranges. While not being bound to any particular theory or mechanism, an increase in ethanol production may be the result of the number or ratio of different types (i.e., variety) of starch hydrolysis products resulting from hydrolysis of starch-containing plant material using at least two different classes of α-amylase enzymes.

In various embodiments, the increase in ethanol yield is at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 3%, at least about 4%, at least about 5%, at least about 6%, at least about 7%, at least about 9% or greater. Even small increases in ethanol yield will translate to large volumes of ethanol produced over time in a commercial-scale fermentation process. Such improvements in ethanol production could result in a significant increase in profit to the ethanol producer.

In another embodiment, the methods disclosed herein result in a lower amount of residual sugar remaining after fermentation when compared to the amount of residual sugar remaining after fermentation of starch-containing plant material that is exposed to only one class of α-amylase enzymes. The amount of residual sugar is reduced by at least about 1%, at least about 2%, at least about 3%, at least about 4%, at least about 5%, at least about 6%, at least about 7%, at least about 9%, at least about 10%, about 15%, about 20%, about 25%, at least about 30% or more. Residual sugar can be measured in terms of total carbohydrate levels or in terms of total glucose levels remaining after, for example, approximately 48 hours of fermentation.

Liquefaction

The methods used for liquefaction of an aqueous slurry of starch-containing plant material vary depending, in part, on the nature of the α-amylase enzymes used in the process as well as the downstream use of the intermediate and end products. The steps can involve a single liquefaction step, or may involve a primary liquefaction, followed by jet cooking and then a secondary liquefaction. The term "secondary liquefaction" refers to a liquefaction process that takes place after an initial period of liquefaction or after a jet cooking step of a multi-stage liquefaction process.

The conditions under which each step is performed also depends on the nature of the enzymes employed. For example, various α-amylase enzymes have different degrees of thermostability and different requirements for pH. The steps should be performed under conditions sufficient for each class of α-amylase to hydrolyze the starch-containing plant material.

As discussed supra, each class of α-amylase enzyme can be provided in the slurry as transgenic plant material expressing one or both classes of α-amylase enzymes, may be provided as a purified or partially-purified enzyme preparation and exogenously added to the slurry, or may be provided in any combination thereof. The slurry may comprise an admixture of a first starch-containing plant material expressing at least a first class of α-amylase, and a second starch-containing transgenic plant material that expresses a second class of α-amylase. Alternatively, the different classes of α-amylase enzymes can be expressed from a single variety of plant that expresses each α-amylase through transformation or breeding. The admixture may further comprise starch-containing plant material that does not express an α-amylase enzyme. Likewise, the admixture may comprise transgenic starch-containing plant material expressing only one class of α-amylase enzyme (where the second class of α-amylase is added exogenously to the slurry) or may consist only of starch-containing plant material that does not express an α-amylase enzyme (where each class of α-amylase is added exogenously to the slurry). The slurry can further comprise an aqueous solution (e.g., water, de-ionized water, backset (i.e., stillage), etc.).

In some embodiments, dry plant materials from different starch-containing plants are mixed together before wetting with the aqueous solution. In other embodiments, the different starch-containing plant materials are added sequentially or simultaneously to a vessel while an aqueous solution is being added.

Where one class of α-amylase is provided in transgenic plant material, and the other class of α-amylase is provided exogenously as a purified or partially-purified enzyme preparation, the initial liquefaction steps may be performed under conditions compatible with the transgenically-expressed α-amylase. The exogenous α-amylase can be added to the slurry during the initial liquefaction steps if the enzyme has similar thermostability and pH optimum characteristics as the transgenically-expressed α-amylase. Alternatively, the exogenous α-amylase can be added in a secondary liquefaction step. This secondary liquefaction step should be performed under conditions sufficient for the exogenous α-amylase to hydrolyze the starch-containing material, which may or may not require adjustment of the pH and/or ion concentrations of the slurry.

Where both classes of α-amylase are added to the slurry exogenously, the liquefaction steps should be compatible with both classes of enzymes, and may require separate liquefaction steps with adjustment of pH and/or ion concentrations between the steps. One of skill in the art will recognize that the pH, ion concentration, temperature, and length of time for each step can be optimized according to the type of α-amylase enzymes employed in the liquefaction as well as the products desired from the liquefaction. Exemplary, non-limiting liquefaction methods are provided below.

It is also contemplated that the different classes of α-amylase can be added to the starch-conversion process simultaneously or sequentially, and each can be added at any step in the process. The invention is also not limited to any particular order in which the different classes of α-amylase are added to the slurry or the liquefact. Where one class of amylase enzymes is provided in a transgenic plant, and one or more additional classes of amylase enzymes is provided as a purified or partially-purified enzyme preparation, the purified or partially-purified enzyme preparation can be added to the transgenic plant material in the initial step(s) of liquefaction, and/or may be added in a subsequent step (including during saccharification or fermentation). Where at least two classes of α-amylase enzymes are provided as transgenic plant material, plant material expressing each enzyme can be provided in the initial step(s) of liquefaction, or the plant material expressing one or more classes of α-amylase can be provided in the initial step(s) and plant material expressing one or more different classes of α-amylases can be provided in one or more subsequent steps. The latter scenario is also contemplated in the event that two or more classes of α-amylase are provided as purified or partially-purified enzyme preparations.

A common enzymatic liquefaction process involves adjusting the pH of a starch slurry to the pH optimum of the α-amylase employed in the methods, with the addition of calcium hydroxide, sodium hydroxide or sodium carbonate. The addition of calcium hydroxide has the advantage of also providing calcium ions which are known to stabilize α-amylases against inactivation. Upon addition of α-amylase (either through provision of transgenic plant material expressing the α-amylase or exogenous addition of α-amylase), the suspension is pumped through a steam jet to instantaneously raise the temperature to between 80° C. to 115° C. The starch is immediately gelatinized and, due to the presence of α-amylase, depolymerized through random hydrolysis of a (1-4) glycosidic bonds by α-amylase to a fluid mass which is easily pumped.

In a second variation to the liquefaction process, α-amylase is added to the starch suspension, the suspension is held at a temperature of 80-100° C. to partially hydrolyze the starch granules, and the partially hydrolyzed starch suspension is pumped through a jet at temperatures in excess of about 105° C. to thoroughly gelatinize any remaining granular structure. After cooling the gelatinized starch, a second addition of α-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using α-amylase. A practice in the art is to undertake enzymatic liquefaction at a lower temperature when using the dry milling process.

Typically, after gelatinization, the starch solution is held at an elevated temperature in the presence of α-amylase until a DE of 10-20 is achieved, usually a period of 1-3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

The heating step of the liquefaction process can also involve the use of temperatures below those used during conventional liquefaction processes (e.g., below about 95° C. to 120° C.). In some embodiments, the first temperature ranges from about 60° C. to about 85° C. In some embodiments, the first temperature ranges from about 75° C. to about 80° C. In other embodiments, the liquefaction does not include a jet—cooking step. In some embodiments, the liquefaction does not include a secondary liquefaction step. Thus, the presently disclosed liquefaction method, in some embodiments, involves a single heating step, or no heating step at all.

In various embodiments, the period of time for each liquefaction step is less than about 180 minutes. In some embodiments, the period of time ranges from about 20 minutes to about 35 minutes. In some embodiments, the first period of time ranges from 22 minutes to 30 minutes (e.g., can be about 22, 23, 24, 25, 26, 27, 28, 29, or 30 minutes).

At each step, the slurry will have a pH that is optimal for the particular α-amylase being employed in that step. Certain α-amylase enzymes are known to function optimally at the natural pH of the slurry (i.e., the pH of the mixture of starch-containing plant material, water, and/or backset). Thus, this slurry can be used without the addition of any pH adjusting chemicals. In some embodiments, this slurry has a pH of between about 4.5 and about 5.2. In some embodiments, the pH is about 4.8.

In some embodiments, jet cooking could be desired. Thus, in some embodiments, the process further comprises a jet cooking step following the heating step. In some embodiments, the jet cooking comprises heating the slurry to a temperature ranging from about 90° C. to about 120° C. for a period of time ranging from about 3 minutes to about 15 minutes.

In order to facilitate wetting or mixing the aqueous slurry, the liquefaction process can include an initial step of holding the slurry in a tank (i.e., a pre-slurry tank) for a period of time prior to the heating step. Any suitable mixing method can be used, including any suitable manual or mechanical mixing method that can be used in conjunction with the pre-slurry and slurry (i.e., liquefaction) tanks. If the slurry is prepared in a separate tank or vessel than that in which the heating will take place, the slurry can be moved to the heating tank by any suitable approach (e.g., pouring, pumping, or the like).

In some embodiments, the starch liquefact prepared from the presently disclosed process has a dextrose equivalent (DE) of at least about 13. In some embodiments, the DE of the liquefact is between about 10 and about 20, or between about 13 to about 17. Thus, the DE of the liquefact can be about 10, 11, 12, 13, 14, 15, 16, 17, 18, 19, or 20.

Ethanol Production

Also provided herein are methods for producing ethanol comprising liquefying an aqueous slurry of starch-containing plant material in the presence of at least a first and a second α-amylase enzyme, wherein the first α-amylase enzyme exhibits a starch hydrolysis pattern that is different from the starch hydrolysis pattern of at least the second α-amylase enzyme to obtain a liquefact; and fermenting the liquefact by yeast to obtain ethanol.

Prior to fermentation, the starch liquefact can be saccharified. The saccharification can include adding one or more starch-digesting enzymes to the starch liquefact during liquefaction (simultaneous liquefaction and saccharification, SLS) or after liquefaction. In some embodiments, the additional starch-digesting enzymes include glucoamylase. Glucoamylases (α-1,4-glucan glucohydrolases, E.C.3.2.1.3.) are starch hydrolyzing exo-acting carbohydrases. Glucoamylases catalyze the removal of successive glucose units from the non-reducing ends of starch or related oligo and polysaccharide molecules and can hydrolyze both linear and branched glucosidic linkages of starch (amylose and amylopectin).

The amount of glucoamylase employed in the present process can vary according to the mixture of dextrins present in the starch liquefact. For example, if the starch liquefact is high in concentration of fermentable, small sugars, less glucoamylase might be needed. The glucoamylase can be provided as transgenic plant material in the initial slurry, or can be added exogenously, or both.

The saccharification process can further include a heating step, wherein the starch liquefact comprising additional starch-digesting enzymes (i.e., the saccharification mixture) is heated to a temperature (e.g., a temperature that allows for optimal activity for the enzymes employed) for a period of time. For example, the starch liquefact can be heated in the presence of an additional starch-digesting enzyme (e.g., glucoamylase) for a period of time from about 5 minutes to about 90 minutes at a temperature from about 60° C. to about 75° C. The temperature can be chosen to be compatible with thermostable glucoamylases, such as those derived from *Thermomyces lanuginosus* (i.e., TlGA).

In some embodiments, the heating step effects complete saccharification of the slurry. Thus, in some embodiments, approximately 100% of the glucose expected from hydrolysis of the starch in the slurry is produced during the heating step.

The glucose produced from a complete SLS process can be recovered by any suitable approach. In addition to glucose, the heated slurry can comprise additional materials, such as oil, protein and fiber by-products of the SLS process. These materials can also have economic value and can be recovered, as well.

The recovered glucose can be prepared in any formulation suitable for fermentation (e.g. to alcohol). The amount of recovered glucose fed into a fermentor can be controlled so as to enhance the survival of the yeast in the fermentor. Alternatively, the glucose can be used in other products, e.g. as a sweetener, in sweetened foods, for intravenous solutions for use in hospitals or other medical settings. The glucose can also be used to prepare other chemicals. For example, the glucose can be treated with glucose isomerase to prepare fructose.

In some embodiments, the heating step effects partial saccharification of the slurry. For example, heating can lead to a mixture containing at least some glucose and some larger dextrins. In some embodiments, the heating step can yield about 90%, 80%, 70%, 60%, 50%, 40%, 30%, 20%, or 10% of the theoretical amount of glucose expected from complete saccharification based upon the amount of starch initially present in the slurry. In some embodiments, the heating provides about 10% saccharification of the slurry. Thus, in some embodiments, the partial saccharification can provide about 10% of the expected amount of glucose expected based upon the amount of starch in the slurry.

Subsequent fermentation of a partially saccharified mixture can be advantageous, in that it allows for control of the initiation, rate, and/or extent of fermentation activity during a SSF process. In particular, the quantity of different starch-containing plant materials and or enzymes can be adjusted to provide a suitable amount of glucose to enhance the survival of yeast during a subsequent fermentation of the mixture resulting from the SLS process. The amount of glucose being fed into a fermentation process can also affect the quality of co-products of the fermentation process, including DDG and DDGS. Alternatively, the glucose resulting from a SLS process can be removed from the mixture and used for any desired purpose.

In some embodiments, the process can include a separate second saccharification step. For example, the process can comprise heating the mixture containing glucose to a second temperature for a second period of time, thereby effecting complete saccharification of the mixture. This second heating step can include the addition of additional enzyme, e.g., additional glucoamylase.

In some embodiments, the mixture from a partial SLS process can be used in a fermentation wherein additional saccharification can take place during fermentation. Thus, in some embodiments both additional enzymes and yeast can be added to the mixture, thereby producing additional glucose and producing ethanol. In some embodiments, the glucose of the presently disclosed process can be used to produce an end product selected from the group consisting of an alcohol, lactic acid, an amino acid, fructose, citric acid, propanediol, DDG, DDGS, or a combination thereof.

Following liquefaction, saccharification, or SLS, the resulting hydrolyzed sugars and starch are fermented. In some embodiments, the fermenting involves a simultaneous saccharification and fermentation (SSF) step. In yet another embodiment, the starch-containing plant material may be used in raw starch fermentation. In the raw starch fermentation, the starch is not liquefied before enzymatic hydrolysis, and the hydrolysis is carried out at a temperature below gelatinization simultaneously with the fermentation process. In one embodiment the invention may be useful in a bacterial or yeast fermentation wherein products from starch hydrolysis are desired. In one embodiment the invention may be useful in a cell free fermentation as described in Allain et al. Journal of Chemical Technology and Biotechnology 82: 117-120 (2007).

In some embodiments, the fermenting comprises adding a solution of yeast to the cooled starch liquefact or raw starch and agitating the cooled starch liquefact at temperature from about 28° C. to about 35° C. for a period of time sufficient for conversion of a sufficient quantity of the sugars to ethanol, e.g., from about 12 to about 72 hours. In some embodiments the yeast is Ethanol Red yeast.

The saccharification and/or fermentation mixture can include additional ingredients to increase the effectiveness of the process. For example, the mixture can include added nutrients (e.g., yeast micronutrients), antibiotics, salts, added enzymes, and the like. Nutrients can be derived from stillage or backset added to the liquid. Suitable salts can include zinc or magnesium salts, such as zinc sulfate, magnesium sulfate, and the like. Suitable added enzymes include those added to conventional processes, such as protease, phytase, cellulase, hemicellulase, exo- and endo-glucanase, xylanase, and the like. In some embodiments, the process comprises adding one or more reagents from the group consisting of an additional starch-digesting enzyme, a yeast extract, an antibiotic, and yeast to the starch liquefact.

The product of the fermentation process can be referred to herein as "beer". For example, fermenting corn produces "corn beer". Ethanol can be recovered from the fermentation mixture (i.e., from the beer) by any of a variety of known processes. For example, ethanol can be recovered by distillation. Thus, in some embodiments, the presently disclosed process further comprises an ethanol recovery step. This step can comprise distillation.

The remaining stillage includes both liquid and solid material. The liquid and solid can be separated by, for example, centrifugation. The recovered liquid, thin stillage, can be employed as at least part of the liquid for forming the saccharification and fermentation mixture for subsequent batches or runs.

The recovered solids, often referred to as distiller's dried grain (DDG), include unfermented grain solids and spent yeast solids. The thin stillage can be concentrated to a syrup, which can be added to the DDG and the mixture then dried to form distiller's dried grain plus solubles (DDGS). DDG and/or DDGS can be sold as animal feed.

The following examples are offered by way of illustration and not by way of limitation.

EXPERIMENTAL

Example 1

Method of Determining the Hydrolysis Pattern and Amount Using an Enzyme Extract

Using alpha amylases from various sources, a series of lab scale liquefaction reactions were conducted using conditions similar to those used in modern 'dry grind' ethanol plants. In the industrial process wherein the alpha amylase as add as a liquid enzyme, ground corn meal are combined with water and a thermotolerant alpha amylase enzymes and, with continuous agitation, the mixtures are heated to approximately 85° C. and held for a period during which the starch is converted to sugars and dextrins of a variety of molecular weights and conformations. Alternatively, when corn amylase is a component in an industrial process, ground corn meal wherein at least a component of the corn meal contains alpha amylase are combined with water and the mixtures are heated as described previously. An instrument from the Mathis company, called the Labomat, was used in this laboratory simulation of industrial liquefaction to control the reaction and maintain constant mixing and a temperature of 85° C.

During the liquefaction reaction the starch within the corn was gelatinized and then hydrolyzed by the various alpha amylase enzymes. The varying degrees and types of hydrolysis products were obtained by the combined effects of dose and type of enzyme used. The analysis of the oligomer profile is analyzed after enzymatic digestion at high temperature and subsequent cooling of the reaction to between 25-30° C. The group of carbohydrate products being evaluated in these experiments are produced by the catalyzed breakdown of starch in a flour of whole corn, followed by the potential formation of retrograde or transglycosylated carbohydrate products created during cooling or through the action of other enzymes present in the corn or enzyme extract. Following the liquefaction reactions a variety of techniques were employed to evaluate the types and relative amounts of sugars liberated from each condition or combination of enzymes.

High Temperature Liquefaction of Ground Corn

After determining the percent moisture of the ground corn, a mixture of corn, water and enzyme was prepared to achieve a mixture with a percent of dry solids of 33.5%. The enzymes used may be derived from various sources. For example as previously described an amylase from a *Bacillus* organism may be used or an alpha-amylase enzyme derived from, containing protein domains from, or sharing sequence homology with a protein isolated from a microorganism of the phylogenic order Thermococcales. Alpha-amylases for example, such as those described in US Patent Publication US2003/0125534 and US2004/0018607 such as D45, BD12870 or 797GL3 may be further characterized in regards to their respective starch hydrolysis pattern and be further employed in starch hydrolysis as described herein. These enzymes may be in crude, partially-purified or purified form and exogenously added to a liquefaction. Alpha-amylases may also be expressed transgenically in a plant essentially as described in Example 3 for 797GL3. Alternatively, D45 or BD12870 DNA sequence can be operably linked to the 27 kD gamma-zein promoter in order to direct expression of the enzyme to endosperm of the seed. In addition, a gamma-zein targeting sequence and an endoplasmic reticulum (ER) retention signal (SEKDEL) can be used to retain the enzyme in the ER organelle. The above described expression cassette can then be incorporated into an agrobacterium transformation vector and transgenic corn plants produced by agrobacterium transformation as described in US 2003-0135885.

A *Bacillus* enzyme was used, including 2.5 µl/gram corn, 5 µl/gram, 7.5 µl/gram, and 10 µl/gram. A total of 200 grams of corn was used to ensure a percent of dry solids of 33.5%. The mixture was then agitated thoroughly to distribute the enzyme and mix the water with the corn flour. The individual reactions with a unique combination of enzyme dose and type were added to 1 L stainless steel beakers used to process the reactions. A Mathis Labomat equipped with a 16 position carousel was used to process the liquefaction reactions. The instrument was programmed to heat the reactions at 6° C./minute and then hold at 85° C. for 1 hour with a continuous rotation of the beakers at 65 rpm, changing direction of rotation every 60 seconds. After liquefaction at high temperature, the reaction is allowed to cool to temperatures between 25-30° C. before analysis for oligomer profiles/concentrations and subsequent fermentation analysis.

The cooked corn slurry was then analyzed using HPLC techniques and the Fehling's assay to characterize the hydrolysis of starches. The results for varying concentrations of the *Bacillus licheniformis* Type XII-A enzyme (Sigma) are shown in Tables 2-5.

Percent Moisture Determination

Using the Mettler HB-43 Moisture Balance the moisture content of a variety of samples can be determined. The majority of samples needing moisture measurement are 'dry' powders. These samples require little special care to determine moisture. However there are special methods that must be followed to achieve the optimal measurements when running samples with a moisture content exceeding 15%. The moisture content of corn flour liquefactions exceeds 60% and has moderate concentrations of sugars and oils that may degrade under high temperature, therefore processing will require the use of supplementary tools. Using glass fiber or other fiber discs from Mettler or Ohaus, moisture will be wicked away from the sample to increase evaporation rate. Low temperatures, <105° C., are to be used for drying samples with high moisture contents or temperature-sensitive samples. Otherwise corn flour and other 'dry' solids can be measured using temperatures up to 130° C. All samples used for moisture determination are terminal samples and should be discarded after use. For more details about the instrument and its operation refer the manufacturer's literature.

The "switch-off criterion" is set to the value of "5" before any measurements are obtained. This switch-off criterion is based on a weight loss per unit of time. As soon as the mean weight loss is less than a preset value during a specified time, the instrument considers drying as complete and automatically discontinues the measurement process. During the drying, the time display shows how long the measurement process has been in progress; the switch-off criterion is inactive during the first 30 sec.

The moisture balance should be set to heat samples at the correct drying temperature. The drying procedure should take between 30 and 40 minutes for slurries at ~105° C. Dry powders usually take 6-8 minutes at 130° C. A 0.75+/–0.01 gram sample of the dry powder is distributed evenly across a clean aluminum pan set in the balance to get an accurate moisture measurement. For slurries, a 10 mL pipette is used to evenly space droplets directly on the aluminum pan totaling 6-8 grams. These drops are then covered lightly by either the filter disc or glass wool and the measurements obtained.

Preparation of Samples for HPLC Analysis

A 50 ml sample of each slurry is placed in a new 50 ml conical bottomed tube. The tubes are centrifuged for 10 minutes at 3,500 rpm. Following the spin, 1.5 ml of the supernatant is removed with a large pipette and added to a new 1.8 ml microcentrifuge tube. The samples are then spun for 10 minutes at 14,000 rpm. The supernatant is then transferred to a Costar Spin-X column and spun in a microcentrifuge for 5 minutes at 5,000 rpm. The filtrate is diluted 1:5 by volume with pure water and used for analysis in HPLC.

Size Exclusion Chromatography

The Waters Alliance HPLC system was used to analyze samples with a technique known as size exclusion chromatography. The general method is flexible and can be adapted to a variety of instruments equipped with other components and conditions. The specific method used for this analysis enabled the separation of soluble sugars produced during liquefaction using the Waters Ultrahydrogel 250 column. The column separated sugars based on size with the largest columns being eluted from the column first. Refractive Index changes are used to produce a signal that is correlated to the concentration of sugars of various sizes being eluted from the column. The instrument was operated with a mobile phase of water at a flow rate of 0.8 ml/minute with the column at a temperature of 45 C and the Refractive Index detector at a temperature of 45 C. An injection of 10 µl of each diluted sample was injected by the instrument and the refractive index monitored over a period of 20 minutes. To estimate the amount of general size of sugars being eluted, a series of sugar standards at known concentrations were processed by the instrument. These standards included solutions of DP1, DP2, DP3, DP4, DP5, DP6, DP7 and dextrins ~DP32, 147 and 300.

Sugar-5 Chromatography

The Waters Breeze HPLC system was used to analyze samples with a technique used currently by industrial ethanol producers to evaluate the amounts of low molecular weight sugars, organic acids, glycerol and ethanol produced during the conversion of grains to ethanol. The general method is flexible and can be adapted to a variety of instruments equipped with other components and conditions. The specific method used for this analysis used a Biorad Aminex HPX-87H Ion Exclusion column for the separation of the aforementioned constituents. Refractive Index changes are used to produce a signal that is correlated to the type and concentration of compounds being eluted from the column. The mobile phase of 5.0 mM was pumped at a rate of 0.6 ml/minute with a column temperature of 60 C and the Refractive Index detector at a temperature of 45° C. An injection volume of 25 ul of each sample (diluted or not) was injected by the instrument and the refractive index monitored over a period of 30 minutes. To estimate the amount and type of compounds being eluted, a series of mixed standards were prepared that contained sugars, dextrins, acetic acid, lactic acid, glycerol and ethanol at known concentrations and were processed by the instrument. The instrument was calibrated using these standards and quantitation achieved by comparison to the linear regression line established for each compound.

Dextrose Equivalent

Standardization of Copper-Tartrate Solution and Preparation of Blank

Exactly 1.0000+0.0001 g of oven-dried dextrose is weighed and transferred quantitatively to a 100-mL volumetric flask, and diluted to volume with RO water. One sample is prepared by adding 5 mL of the 1% glucose solution to a 500-mL beaker containing 20 mL water. Then a blank is prepared with 25 mL of water in a 500 mL flask. Fehlings Solution A (10.0+0.1 mL) is accurately measured and added into each beaker. Then Fehlings Solution B (10.0+0.1 mL) is accurately measured and added into each beaker. Each beaker is swirled to mix thoroughly. Several glass beads are placed into each beaker. Each beaker is heated on a hot plate until the solution boils for 3-4 minutes. Each beaker is removed from the hot plate and cooled in a cold tap water bath. After cooling, 10.0+0.1 mL KI solution and 10.0+0.1 mL of H2SO4 solution are added, in order, and the beakers are swirled. Each sample is titrated with 0.1N sodium thiosulfate solution until a light straw color is reached. Two milliliters of starch indicator is added and titrated until the sample turns a milky white. The titration volume is recorded.

Sample Assay—Manual Titration

When determining the DE for a liquefied corn flour sample it is necessary to use the correct amount of sample so as not to overload the assay. This amount is expressed in terms of mass of dry carbohydrate. When using Maltrin or other pure carbohydrate samples, the moisture content is determined using a moisture balance and the mass added to the assay is corrected for that moisture value. The corn flour liquefact is diluted before a sample is taken for use in this method. To determine the amount of a corn or carbohydrate sample needed to obtain an accurate result from the Fehling's assay, the protocol in Appendix I is used.

A 500-mL flask is placed on the analytical balance and the balance calibrated. The sample is weighed into a beaker and the weight recorded to 4 decimal places. (Table 1 lists mass of carbohydrate for given DE ranges of dried product). Three beakers are prepared for Maltrin MD105, 150 and 250 maltodextrins. These serve as internal controls to monitor assay performance.

Enough reverse osmosis (RO) water is added to bring the total volume to approximately 25 mL. The beaker is swirled to ensure that the sample is completely dissolved/mixed. Fehlings Solution A (10.0 mL) is accurately measured and added into each beaker. Then Fehlings Solution B (10.0 mL) is accurately measured and added into each sample flask. Each beaker is swirled to mix thoroughly. Several glass beads are placed into each beaker. Each sample beaker is heated on a hot plate until the solution boils for 3-4 minutes. (Approximately 7 minutes total time) Each beaker is removed from the hot plate and cooled in a cold water bath. After cooling, 10.0+0.1 mL of the KI solution and 10.0+0.1 mL of the $H_2SO_4$ solution are added, in order, and the beakers are swirled. Each sample is titrated with 0.1N sodium thiosulfate solution until a light straw color is reached. 2 mL of starch indicator is titrated into the sample until the sample turns a milky white. The titration volume is recorded.

Calculation of Dextrose Equivalent:

Two calculations are included for the determination of DE from the Fehling's method:

$$\text{Dextrose Equivalent (Carbohydrate Only)} = \frac{500 \times (\Delta \text{ titrate of blank} - \Delta \text{ titrate of sample})}{(\text{Dry Carbohydrate mass gm}) \times 100 \times (\Delta \text{ titrate of blank} - \Delta \text{ titrate of standard})}$$

$$\text{Dextrose Equivalent (No Carbohydrate Correction)} = \frac{500 \times (\Delta \text{ titrate of blank} - \Delta \text{ titrate of sample})}{((\text{Total dry mass in grams}) \times 100 \times (\Delta \text{ titrate of blank} - \Delta \text{ titrate of standard})}$$

*dry *carbo*. mass = (total dry mass) × (% starch composition of sample)

Appendix I

This assay will determine the amount of reducing ends in a sample that contains carbohydrates. To calculate DE, the percentage of carbohydrates contained within a sample is required to determine the correct value. There is a maximum amount of reducing ends that can be present in a sample while providing accurate and useful data using the Fehling's method. A sample that is mostly small sugars will have a high DE value and will require significantly less mass to fall within the working range of this assay when compared with a sample that has mostly high molecular weight sugars, maltodextrins or small starch molecules. If the sample is suspected to contain mostly small sugars and is not diluted properly then the assay will be saturated before titration begins.

Table 1 provides a quick reference to determine the correct dry sample mass for use in the Fehling's method by using an estimate of the DE value. For samples with unknown DE values, a very small mass of approximately 0.1 g is used for initial titrations. When using a pure carbohydrate sample, the mass of dry sample to use in this method is obtained from column 2 of Table 1. If using corn or other types of grain flour column 3 provides the correct mass of a sample to use.

The procedures in this protocol have been modified to measure DE from corn flour liquefactions (cooked wet slurries at 20 to 35% dry solids). Some liquefacts are hydrolyzed to DE's in excess of 30 and therefore a very small sample can be used effectively. Through employment of a dilution scheme, a solution with corn flour can be obtained in suspension where the equivalent of 0.1-1 grams of dry flour is present in a given volume, usually 3-5 mL, and then added to the assay to keep the sample within the dynamic range. The corn flour liquefact should be diluted 1:20 by mass to achieve a solution that will be dilute enough to allow for the determination of DE values >25. If the 1:200 dilution is used for this assay up to 25 mL of the dilution can be used as a sample.

A 10 gram dry flour sample is mixed with water or other additives and liquefied. The percent solids or percent moisture is determined and used to determine what the 10 gram sample of flour now weighs in the presence of water. For example, if 10 grams of flour was liquefied at 30% solids the mass of a 10 gram dry flour equivalent of liquefact is (10 g dry flour*100)/30=33.3 g. Therefore 33.3 grams of the wet liquefact at 30% solids represents 10 g of dry flour. This 33.3 grams will then be diluted to 200 grams with water. This represents an effective 1:20 dilution of corn flour [(10 g dry flour)/(166.7 g of H2O+33.3 g corn slurry)]. From this 1:20 dilution an aliquot of the suspension is taken and used directly in the Fehling's method. The beaker in which the assay is run is zeroed on a balance. To the beaker is added enough diluted liquefact to equal the equivalent of 0.1-1.0 g of dry flour mass depending of expected DE utilizing Table 1.

It is important to determine the true mass of corn flour or other carbohydrate source going into the assay so a balance capable of reading to the 0.0001 g is required. From the dilution, up to 25 mL can be used but the mass must be determined very accurately to back calculate the mass of corn flour. For standards or dry compounds, the mass can be weighed directly into the beaker, skipping the dilution series.

TABLE 1

Mass of Substance For Use in the Fehling's Method

| Expected DE | Dry mass of pure carbohydrate (g) | Dry mass of corn flour (g) |
|---|---|---|
| 4-7 | 0.90 | 1.29 |
| 8-12 | 0.45 | 0.64 |
| 13-17 | 0.30 | 0.43 |
| 17-20 | 0.22 | 0.31 |
| 20-23 | 0.20 | 0.29 |
| 23-27 | 0.16 | 0.23 |
| 26-100 | 0.10 | 0.14 |

Useful Equations for corn slurry liquefact:

Dry mass of flour present in wet corn flour liquefact slurry at (x) % dry solids=Dry flour mass= [(Wet wgt. of liquefact)×(% dry solids of liquefact)]/100

Mass of wet liquefact that represents (x) g of dry flour at (x) % dry solids=Wet wt. of liquefact= [(Dry flour wgt.)×100]/percent dry solids of liquefact Total dry mass=diluted sample mass (gm)/dilution factor Dry carbohydrate mass (gm)=Total dry mass (gm)* % starch composition Post-Liquefaction Oligosaccharide Distribution:

Size exclusion chromatography on liquefacts from Corn Amylase (797GL3) (described in Example 2) and commercially available α-amylases clearly demonstrate the novel action pattern of both 797GL3 and D45 vs conventional amylases derived from bacterium of the *Bacillus* genus. Both Corn Amylase (797GL3) and D45 hydrolyze starch to smaller fragments than *Bacillus* amylases. The consequence of the different breakdown pattern is manifested primarily during saccharification—fermentation.

The ethanol industry typically will use the Fehling's assay or equivalent test to determine the Dextrose Equivalent (DE) for the slurry produced during the liquefaction process. Using liquid α-Amylase enzymes a producer will try to generate corn slurry that has a DE between 10 and 15. When the a slurry with a DE of between 10 and 15 is analyzed using Size Exclusion Chromatography the pattern of various sized sugars and dextrins generated by the enzyme can be visualized as it elutes from the column.

The pattern produced using α-Amylases derived from bacterium of the *Bacillus* genus are very similar to each other and very different from those produced using either 797GL3/Corn Amylase or D45 (FIG. 1 of Atichokudomchai et al. (2006) *Carbohydrate Polymers* 64:582-588). Liquefied corn produced by liquefaction with *Bacillus* α-Amylases typically have a substantial fraction of products that range from DP32 to DP300 where liquefacts derived from Corn Amylase have almost no sugars in this size range. A bimodal molecular weight distribution has been observed when analyzing hydrolysates of starch using *Bacillus* alpha amylase compared to as unimodal distribution observed when using Corn Amylase.

Dionex Ion Exchange Chromatography

Ion exchange chromatography was performed according the MacGregor et al. (1994) Carbohydrate Research 2.57; 249-268, which is herein incorporated by reference in its entirety.

Differences exist between oligomer profile patterns generated from liquefacts produced with either *Bacillus* amylases or Corn Amylase. The *Bacillus* amylases produce a pattern with clearly defined and evenly spaced peaks, while not to be limited by theory, the evenly spaced peaks likely representing linear chains of oligomers and also possess a single peak of rather high but unknown molecular weight. The pattern produced with Corn Amylase alone shows a very different pattern with many intermediate peaks and a lack of the high molecular weight peaks. See FIG. 4. This pattern is similar to the results shown for the proposed reaction pattern described in Atichokidomachai et al. (see FIG. 5 therein) demonstrating differences in products from *Bacillus* amylases and D45.

Example 2

Method of Making Corn Amylase

The terms corn amylase, CA, and corn amylase (797GL3) refer to corn plants expressing the α-amylase enzyme 797GL3. The enzyme is described in US Patent Publication US2003/0125534 and US2004/0018607, which are herein incorporated by reference in their entirety. Methods of making corn plants expressing 797GL3 is described in US 2003-0135885. As described similarly in US 2003-0135885, corn amylase comprises an expression cassette wherein a nucleotide sequence encoding the enzyme, 797GL3, was operably linked to the 27 kD gamma-zein promoter in order to direct expression of the enzyme to endosperm of the seed. In addition, a gamma-zein targeting sequence and an endoplasmic reticulum (ER) retention signal (SEKDEL) was used to retain the enzyme in the ER organelle. The above described expression cassette was incorporated into an agrobacterium transformation vector and transgenic corn plants produced by agrobacterium transformation as described in US 2003-0135885.

Example 3

Use of Two Thermotolerant α-Amylases During Liquefaction to Improve the Production of Ethanol with Saccharomyces Cervisae and Corn Milled corn was liquefied for 1 hour at 85 C in the Mathis labomat at pH 5.8 at 33% dry solids. No thin stillage or other adjuncts were added to the liquefact. Varying combinations of alpha amylase enzymes were used during the process and the DE was kept near constant for all conditions. A 'benchmark' dose of Bacillus enzyme was determined to produce a DE of 10-15, 0.1 μl/dry gram, and then used a control. The corresponding dose of Corn Amylase to produce a similar DE, 5% admix was also used as a control. Three combinations of Corn Amylase and Bacillus were used for the evaluation, 0.09 μl/dry gram Bacillus+0.5% admix of Corn Amylase (797GL3), 0.05 μl/dry gram Bacillus+2.5% admix Corn Amylase and 0.01 μl/dry gram Bacillus+4.5% admix Corn Amylase. For each condition, 200 grams of flour were liquefied in large labomat beakers. Moisture was determined by using a Mettler Moisture Balance set at 105 C for ~20 minutes until weight loss <0.01 g/min.

Following liquefaction the slurry was allowed to cool to room temperature. From each reaction vessel three replicate fermentation reactions were assembled. The nutrient source was a concentrated solution of yeast extract dissolved in water with gentle heating. The antibiotic used was tetracycline dissolved at 10 mg/ml in 95% Ethanol. The glucoamylase used was derived from Aspergillus niger and is commercially available from Sigma, produced by Novozymes Corp. After all of the ingredients were added to a 100 ml glass bottle, the cap was tightly closed, shaken vigorously for 30 seconds and then the cap was opened minimally to vent evolved gases. The fermentations were then placed in a 32 C walk in incubator for 72 hours.

Small amounts of the slurry were analyzed using the BCA method to determine DE (Dextrose Equivalent) (Table 2). A small aliquot was used for HPLC analysis using the Sugar 5 method and Size Exclusion Chromatography to quantify and qualify the amount and distribution of soluble carbohydrates. An aliquot was also analyzed using the Dionex system equipped with an ion exchange column to qualify individual sugars, branched and linear, up to DP40.

TABLE 2

| | DE determination via BCA assay | | | | |
|---|---|---|---|---|---|
| | Sample # | | | | |
| | 1 | 2 | 3 | 4 | 5 |
| Sample label | Bac 0.10 ul/g | Bac 0.09 ul/g + 0.5% CA | Bac 0.50 ul/g + 2.5% CA | Bac 0.01 ul/g + 4.5% CA | 5% CA |
| Relative concentration of glucose (μg/mL) | 177.718 | 186.832 | 208.043 | 278.926 | 272.31 |
| Initial dilution (mL) | 400.62 | 401.05 | 400.22 | 400.65 | 400.49 |
| final dilution ratio | 100 | 100 | 100 | 100 | 100 |
| % DS | 33 | 33 | 33 | 33 | 33 |
| mass of slurry | 60.44 | 60.45 | 60.81 | 60.45 | 61.06 |
| Flour (g) | 19.9452 | 19.9485 | 20.0673 | 19.9485 | 20.1498 |
| glucose (g/L) | 0.03198924 | 0.03362976 | 0.03744774 | 0.05020668 | 0.049016 |
| glucose (g) | 1.281552933 | 1.348721525 | 1.49873345 | 2.011530634 | 1.963034 |
| starch (g) [corn 71% starch] | 14.21305008 | 14.21540168 | 14.30005916 | 14.21540168 | 14.35885 |
| DE | 9.016734095 | 9.487748254 | 10.48061014 | 14.15036085 | 13.67125 |

Additionally a small amount of liquefact was spiked with a high dose of Glucoamylase ~2 ml/75 g and 0.1 gm Sodium azide and incubated for 144 hrs at 32 C to observe the ability of each condition to saccharify.

Conditions using both amylases show an increase in the amount of ethanol produced at 48 hours with the two controls (CA5.0% and Bac 0.1 ul/g) being essentially equal (Table 3).

TABLE 3

Ethanol production

| Timepoint (in hours) | Bac 0.1 ul/g | Bac 0.09 ul/g + CA0.5% | Bac 0.05 ul/g + CA2.5% | Bac 0.01 ul/g + CA4.5% | CA5.0% |
|---|---|---|---|---|---|
| 0 | 0 | 0 | 0 | 0 | 0 |
| 23.5 | 15.583 | 15.757 | 15.711 | 15.662 | 15.666 |
| 36 | 17.189 | 17.265 | 17.032 | 17.151 | 17.220 |
| 48 | 18.253 | 18.305 | 18.345 | 18.297 | 18.232 |
| 72 | 18.406 | 18.454 | 18.476 | 18.478 | 18.439 |

Another technique used to evaluate the amount of consumed carbohydrates is to look at residual soluble sugars, again the combination of the two amylases produces amount lower that the *Bacillus* alpha amylase but not quite as low as Corn Amylase (Tables 4 and 5). Total residual starch can be measured as described in Xiong, Y et al, Journal of Animal Science 63: 3861 or AOAC method 996.11 herein incorporated by reference.

TABLE 4

Total residual sugars

| Timepoint (in hours) | Bac 0.1 ul/g | Bac 0.09 ul/g + CA0.5% | Bac 0.05 ul/g + CA2.5% | Bac 0.01 ul/g + CA4.5% | CA5.0% |
|---|---|---|---|---|---|
| 0 | 29.727 | 26.9 | 26.96 | 26.887 | 26.894 |
| 23.5 | 2.811 | 2.695667 | 2.862667 | 2.846667 | 2.672667 |
| 36 | 1.139 | 1.160333 | 1.125667 | 1.158 | 1.017 |
| 48 | 0.756667 | 0.769667 | 0.702333 | 0.680667 | 0.665333 |
| 72 | 0.912 | 0.897 | 0.664333 | 0.563667 | 0.564667 |

TABLE 5

Total glucose

| Timepoint (in hours) | Bac 0.1 ul/g | Bac 0.09 ul/g + CA0.5% | Bac 0.05 ul/g + CA2.5% | Bac 0.01 ul/g + CA4.5% | CA5.0% |
|---|---|---|---|---|---|
| 0 | 0.689 | 0.672 | 0.692 | 0.647 | 0.626 |
| 23.5 | 1.589 | 1.291 | 1.255 | 1.179 | 1.110 |
| 36 | 0.135 | 0.116 | 0.160 | 0.163 | 0.125 |
| 48 | 0.053 | 0.055 | 0.033 | 0.024 | 0.017 |
| 72 | 0.279 | 0.251 | 0.216 | 0.192 | 0.184 |

Example 4

Measurement of Viscosity Using Two Thermotolerant α-Amylases During Liquefaction To characterize the effects two amylase liquidfaction on viscosity, a series of experiments were carried out using a unimodal and bimodal amylase. Unimodal amylases comprised 797GL3, D45, and BD12870. Amylases exhibiting a bimodal hydrolysis patterns consisted of amylase derived from a *Bacillus* organism. A 30% total solid liquefaction sample from a large dry grind ethanol plant was collected and frozen. The sample was treated with a *Bacillus* amylase prior to collection. Upon time for analysis, the samples were defrosted at room temperature and 4×40 ml aliquots were prepared in 50 ml conical tubes. Viscosity was measured using a RVA-4 viscometer (Newport Scientific). To measure viscosity, the samples are first heated up in a water bath to 85° C. Following, 25 grams of each sample is weighed out and placed into a viscometer vessel and capped. These samples are then placed into the Newport Scientific Rapid Visco Analyzer (RVA) and the paddle speed is set to 160 RPM. Instrument settings are such that the samples will be heated to 85° C. and held for 5 minutes. RVA will then be ramped down over 5 minutes to 32° C. Samples will then be held at 32° C. for 5 minutes. Total run time is therefore 15 minutes. Viscosity data is collected throughout the 15 minute time period. Table 6 demonstrates the data points at minimum viscosity at 2-4 minutes at 85° C. and maximum viscosity is acquired between 12-14 minutes at 32° C.

The first tube, control #1, was raised to 85° C. and 25 grams of mash is weighed out into a viscometer vessel and measured for viscosity as described above. The second tube, control #2 was heated at 85° C. for 90 minutes, then acid stopped with 400 µl of 40% $H_2SO_4$, and tested for viscosity. The purpose of control #2 is to determine if any additional liquid *Bacillus* amylase activity would remain during additional cooking of the frozen mash sample. The third tube, spiked CA protein, was prepared by adding 450 µl of a purified corn amylase protein extract (1 mg protein/ml of 20% ethanol) to achieve an approximate 10× dose. The third tube was raised to 85° C. for 90 minutes, then acid stopped with 400 µl of 40% $H_2SO_4$, and tested for viscosity. The forth tube, spiked D45 liquid amylase, was prepared by adding 30 µl of formulated enzyme to achieve a approximate 10× dose and measured for viscosity. The forth tube, spiked BD12870 liquid amylase, was prepared by adding 500 µl of formulated enzyme. A drop in viscosity is observed for those samples where a unimodal amylase has been added to the liquefact containing a *Bacillus* amylase (See Table 6 for viscosity results).

TABLE 6

Viscosity measurements

| Sample | MIN AT 85° C. | MAX AT 32° C. |
|---|---|---|
| control 1 | 197 | 442 |
| control 2 | 183 | 366 |
| 450 uL CA | 126 | 238 |
| 30 uL D45 | 116 | 229 |
| 500 uL BD12870 | 149 | 298 |

Example 5

Additional Assays for Measuring Starch Liquefaction

To further characterize the unique hydrolysis patterns associated with each individual group of alpha amylase enzymes, either those from *Bacillus* bacterium or Corn Amylase, and those created through the use of combinations of members of the two groups, a series of liquefaction experiments are performed. Other amylases such as BD12870, *Thermococcales* derived amylases, unimodal or bimodal amylases may be combined essentially as described in Example 3 to show a synergistic dual mode of action benefit.

Using available alpha amylase enzymes and ground corn, amylose, amylopectins and purified corn starch as substrates, hydrolysis is performed using conditions that are similar to those used in ethanol production facilities. Additionally, conditions that are not currently being used for industrial processes can be utilized, especially ones that may offer additional process efficiencies or yield advantages not attainable through the use of a single enzyme. These conditions may include liquefaction at pH<5.8, very short liquefaction times <1 hour, lower temperature of liquefaction, the elimination of the jet cooking process, liquefaction of slurry that has a very high percent of dry solids (e.g., >33.5%). The same general protocol for generating liquefact at a lab scale as described previously is used. To further validate the synergistic effects of using two amylases of divergent hydrolytic action patterns, samples produced from a full scale industrial plant can be analyzed to compare the performance of the two enzymes alone or in concert with results obtained from lab scale experiments.

For each of these liquefacts the degree of hydrolysis is measured using the Fehling's assay or equivalent technique to determine Dextrose Equivalent. Additionally liquid chromatographic analysis is used to characterize the profile of oligomers generated through hydrolysis, both quantitatively and qualitatively. Samples from large scale dry ethanol fermentations may also be collected and analyzed as described by Examples 1-6.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for starch liquefaction, the method comprising: liquefying an aqueous slurry of starch-containing plant material in the presence of at least a first and a second class of α-amylase enzymes to obtain a liquefact, wherein the first class of α-amylase enzymes exhibits a unimodal starch hydrolysis pattern and is derived from a microorganism of the order Thermococcales and the second class of α-amylase enzymes exhibits a bimodal starch hydrolysis pattern, and wherein the at least first and second class of α-amylase enzymes in the liquefact produces an increased amount of ethanol at 48 hours compared to a single class of enzyme.

2. The method of claim 1, wherein the second class of α-amylase enzymes is derived from a *Bacillus* species.

3. The method of claim 1, wherein said starch-containing plant material comprises transgenic plant cells comprising a polynucleotide encoding at least the first class of α-amylase enzymes, and wherein the method comprises one or more liquefaction steps that are performed under conditions sufficient for the encoded first class of α-amylase enzymes to hydrolyze said starch-containing plant material.

4. The method of claim 1, wherein at least the first class of α-amylase enzymes is exogenously-added, and wherein the process comprises one or more liquefaction steps that are performed under conditions sufficient for the first class of α-amylase enzymes to hydrolyze said starch-containing plant material.

5. The method of claim 3, wherein said starch-containing plant material comprises transgenic plant cells comprising a polynucleotide encoding at least the second class of α-amylase enzymes, and wherein the process comprises one or more liquefaction steps that are performed under conditions sufficient for the encoded first and second classes of α-amylase enzymes to hydrolyze said starch-containing plant material.

6. The method of claim 3, wherein the second class of α-amylase enzymes are exogenously-added, and wherein the method comprises one or more liquefaction step that are performed under conditions sufficient for the first and the second classes of α-amylase enzymes to hydrolyze said starch-containing plant material.

7. The method of claim 4, wherein at least the second class of α-amylase enzymes comprises exogenously-added enzymes to the slurry in one or more liquefaction steps that are performed under conditions sufficient for each of the first and the second classes of α-amylase enzymes to hydrolyze said starch-containing plant material.

8. The method of claim 2, wherein the starch-containing plant material is obtained from a plant selected from the group consisting of rice, barley, potato, sweet potato, canola, sunflower, rye, oats, wheat, corn, soybean, sugar beet, tobacco, *Miscanthus* grass, Switch grass, safflower, trees, cotton, cassava, tomato, sorghum, alfalfa and sugarcane.

9. The method of claim 3, wherein the starch-containing plant material is obtained from a corn plant.

10. The method of claim 1, wherein the bimodal starch hydrolysis pattern and the unimodal starch hydrolysis pattern are determined by analyzing the distribution of oligosaccharides resulting from hydrolysis of starch by each of the α-amylase enzymes to a dextrose equivalent (DE) of between 10 and 15.

11. The method of claim 10, wherein hydrolysis of starch by the first class of α-amylase enzyme exhibiting a unimodal starch hydrolysis pattern results in a majority of hydrolysates that are in a lower size range.

12. The method of claim 11, wherein the lower size range is from DP1 to DP30.

13. The method of claim 10, wherein hydrolysis of starch by the second class of α-amylase enzyme exhibiting a bimodal starch hydrolysis pattern results in hydrolysates that are in both the lower size range and a higher size range.

14. The method of claim 13, wherein the lower size range is from DP1 to DP30.

* * * * *